United States Patent
Ni et al.

(10) Patent No.: US 9,931,074 B2
(45) Date of Patent: Apr. 3, 2018

(54) CARDIAC RESYNCHRONIZATION THERAPY FOR IMPROVED HEMODYNAMICS BASED ON DISORDERED BREATHING DETECTION

(71) Applicant: Cardiac Pacemakers, Inc., St. Paul, MN (US)

(72) Inventors: Quan Ni, Shoreview, MN (US); Douglas R. Daum, Woodbury, MN (US); Jeffrey E. Stahmann, Ramsey, MN (US); Kent Lee, Iowa City, IA (US); Jesse W. Hartley, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/233,369

(22) Filed: Aug. 10, 2016

(65) Prior Publication Data
US 2016/0345897 A1 Dec. 1, 2016

Related U.S. Application Data

(63) Continuation of application No. 11/282,963, filed on Nov. 18, 2005, now abandoned.

(51) Int. Cl.
*A61N 1/365* (2006.01)
*A61B 5/00* (2006.01)
(Continued)

(52) U.S. Cl.
CPC .............. *A61B 5/4836* (2013.01); *A61B 5/02* (2013.01); *A61B 5/0472* (2013.01); *A61B 5/08* (2013.01); *A61B 5/4818* (2013.01); *A61B 5/6846* (2013.01); *A61N 1/3627* (2013.01); *A61N 1/36521* (2013.01)

(58) Field of Classification Search
None
See application file for complete search history.

(56) References Cited

U.S. PATENT DOCUMENTS 4,091,818 A 5/1978 Brownlee et al.
4,414,982 A 11/1983 Durkan
(Continued)

FOREIGN PATENT DOCUMENTS

EP 0770407 A1 5/1997
EP 0940155 A3 9/1999
(Continued)

OTHER PUBLICATIONS

"Aircraft Noise and Sleep Disturbance: final report", prepared by the Civil Aviation Authority London on behalf of the Department of Trade, CAA Report, http://www.caa.co.uk/docs/33/ERCD %208008.pdf, (dated Aug. 1980).
(Continued)

*Primary Examiner* — Deborah Malamud
(74) *Attorney, Agent, or Firm* — Schwegman Lundberg & Woessner P.A.

(57) ABSTRACT

The presence of disordered breathing is detected using an implantable medical device. A cardiac condition is detected that is indicative of the patient's cardiac status. Based on the presence of disordered breathing and the cardiac condition, the patient is identified as suitable for a cardiac resynchronization therapy.

20 Claims, 10 Drawing Sheets

(51) Int. Cl.
    *A61N 1/362*     (2006.01)
    *A61B 5/02*     (2006.01)
    *A61B 5/0472*     (2006.01)
    *A61B 5/08*     (2006.01)

(56) References Cited

U.S. PATENT DOCUMENTS

| | | |
|---|---|---|
| 4,562,841 A | 1/1986 | Brockway et al. |
| 4,562,842 A | 1/1986 | Morfeld et al. |
| 4,813,427 A | 3/1989 | Schlaefke et al. |
| 4,827,935 A | 5/1989 | Geddes et al. |
| 4,830,008 A | 5/1989 | Meer |
| 4,836,219 A | 6/1989 | Hobson et al. |
| 4,856,524 A | 8/1989 | Baker, Jr. |
| 4,928,688 A | 5/1990 | Mower |
| 4,953,551 A | 9/1990 | Mehra et al. |
| 5,024,222 A | 6/1991 | Thacker |
| 5,036,849 A | 8/1991 | Hauck et al. |
| 5,105,354 A | 4/1992 | Nishimura |
| 5,133,353 A | 7/1992 | Hauser |
| 5,146,918 A | 9/1992 | Kallok et al. |
| 5,170,784 A | 12/1992 | Ramon et al. |
| 5,178,156 A | 1/1993 | Takishima et al. |
| 5,179,945 A | 1/1993 | Van Hofwegen et al. |
| 5,187,657 A | 2/1993 | Forbes |
| 5,203,348 A | 4/1993 | Dahl et al. |
| 5,209,229 A | 5/1993 | Gilli |
| 5,211,173 A | 5/1993 | Kallok |
| 5,215,082 A | 6/1993 | Kallok et al. |
| 5,230,337 A | 7/1993 | Dahl et al. |
| 5,233,983 A | 8/1993 | Markowitz |
| 5,245,995 A | 9/1993 | Sullivan et al. |
| 5,261,400 A | 11/1993 | Bardy |
| 5,280,791 A | 1/1994 | Lavie |
| 5,284,136 A | 2/1994 | Hauck et al. |
| 5,292,338 A | 3/1994 | Bardy |
| 5,299,118 A | 3/1994 | Martens et al. |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,331,966 A | 7/1994 | Bennett et al. |
| 5,334,222 A | 8/1994 | Salo et al. |
| 5,335,657 A | 8/1994 | Terry, Jr. et al. |
| 5,360,442 A | 11/1994 | Dahl et al. |
| 5,366,496 A | 11/1994 | Dahl et al. |
| 5,372,606 A | 12/1994 | Lang et al. |
| 5,376,103 A | 12/1994 | Anderson et al. |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,438,969 A | 8/1995 | Kurr et al. |
| 5,439,482 A | 8/1995 | Adams et al. |
| 5,441,518 A | 8/1995 | Adams et al. |
| 5,466,245 A | 11/1995 | Spinelli et al. |
| 5,468,254 A | 11/1995 | Hahn et al. |
| 5,476,485 A | 12/1995 | Weinberg et al. |
| 5,485,851 A | 1/1996 | Erickson |
| 5,520,176 A | 5/1996 | Cohen |
| 5,520,191 A | 5/1996 | Karlsson et al. |
| 5,522,862 A | 6/1996 | Testerman et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,601,607 A | 2/1997 | Adams |
| 5,603,732 A | 2/1997 | Dahl et al. |
| 5,620,466 A | 4/1997 | Haefner et al. |
| 5,634,938 A | 6/1997 | Swanson et al. |
| 5,641,326 A | 6/1997 | Adams |
| 5,645,570 A | 7/1997 | Corbucci |
| 5,662,688 A | 9/1997 | Haefner et al. |
| 5,697,953 A | 12/1997 | Kroll et al. |
| 5,704,365 A | 1/1998 | Albrecht et al. |
| 5,713,355 A | 2/1998 | Richardson et al. |
| 5,713,933 A | 2/1998 | Condie et al. |
| 5,724,984 A | 3/1998 | Arnold et al. |
| 5,738,102 A | 4/1998 | Lemelson |
| 5,792,188 A | 8/1998 | Starkweather et al. |
| 5,802,188 A | 9/1998 | Mcdonough |
| 5,814,087 A | 9/1998 | Renirie |
| 5,827,326 A | 10/1998 | Kroll et al. |
| 5,836,987 A | 11/1998 | Baumann et al. |
| 5,844,680 A | 12/1998 | Sperling |
| 5,855,593 A | 1/1999 | Olson et al. |
| 5,891,023 A | 4/1999 | Lynn |
| 5,895,414 A | 4/1999 | Sanchez-Zambrano |
| 5,902,250 A | 5/1999 | Verrier et al. |
| 5,911,218 A | 6/1999 | Dimarco |
| 5,916,243 A | 6/1999 | KenKnight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,970,975 A | 10/1999 | Estes et al. |
| 5,974,340 A | 10/1999 | Kadhiresan |
| 5,981,011 A | 11/1999 | Overcash |
| 5,997,526 A | 12/1999 | Giba et al. |
| 6,026,320 A | 2/2000 | Carlson et al. |
| 6,044,298 A | 3/2000 | Salo et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,115,628 A | 9/2000 | Stadler et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,148,230 A | 11/2000 | Kenknight |
| 6,148,233 A | 11/2000 | Owen et al. |
| 6,190,326 B1 | 2/2001 | McKinnon et al. |
| 6,200,265 B1 | 3/2001 | Walsh et al. |
| 6,205,357 B1 | 3/2001 | Ideker |
| 6,221,011 B1 | 4/2001 | Bardy |
| 6,227,072 B1 | 5/2001 | Ritchey et al. |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,275,727 B1 | 8/2001 | Hopper et al. |
| 6,277,072 B1 | 8/2001 | Bardy |
| 6,280,380 B1 | 8/2001 | Bardy |
| 6,280,462 B1 | 8/2001 | Hauser et al. |
| 6,280,680 B1 | 8/2001 | Liang et al. |
| 6,285,907 B1 | 9/2001 | Kramer et al. |
| 6,312,378 B1 | 11/2001 | Bardy |
| 6,327,499 B1 | 12/2001 | Alt |
| 6,336,903 B1 | 1/2002 | Bardy |
| 6,351,669 B1 | 2/2002 | Hartley et al. |
| 6,351,670 B1 | 2/2002 | Kroll |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,361,494 B1 | 3/2002 | Lindenthaler |
| 6,363,270 B1 | 3/2002 | Colla et al. |
| 6,368,284 B1 | 4/2002 | Bardy |

(56) References Cited

U.S. PATENT DOCUMENTS

| | | |
|---|---|---|
| 6,368,287 B1 | 4/2002 | Hadas |
| 6,371,922 B1 | 4/2002 | Baumann et al. |
| 6,375,621 B1 | 4/2002 | Sullivan |
| 6,398,728 B1 | 6/2002 | Bardy |
| 6,405,085 B1 | 6/2002 | Graupner et al. |
| 6,409,675 B1 | 6/2002 | Turcott |
| 6,411,848 B2 | 6/2002 | Kramer et al. |
| 6,415,174 B1 | 7/2002 | Bebehani et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,459,929 B1 | 10/2002 | Hopper et al. |
| 6,463,325 B1 | 10/2002 | Bolz |
| 6,480,733 B1 | 11/2002 | Turcott |
| 6,487,443 B2 | 11/2002 | Olson et al. |
| 6,490,485 B1 | 12/2002 | Sun et al. |
| 6,491,639 B1 | 12/2002 | Turcott |
| 6,491,675 B1 | 12/2002 | Shimada et al. |
| 6,496,715 B1 | 12/2002 | Lee et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,574,507 B1 | 6/2003 | Bonnet |
| 6,584,351 B1 | 6/2003 | Ekwall |
| 6,589,188 B1 | 7/2003 | Street et al. |
| 6,597,951 B2 | 7/2003 | Kramer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,641,542 B2 | 11/2003 | Cho et al. |
| 6,708,058 B2 | 3/2004 | Kim et al. |
| 6,752,765 B1 | 6/2004 | Jensen et al. |
| 6,752,766 B2 | 6/2004 | Kowallik et al. |
| 6,760,615 B2 | 7/2004 | Ferek-Petric |
| 6,766,190 B2 | 7/2004 | Ferek-Petric |
| 6,773,404 B2 | 8/2004 | Poezevera |
| 6,810,287 B2 | 10/2004 | Zhu et al. |
| 6,823,214 B1 | 11/2004 | Sun et al. |
| 6,839,593 B1 | 1/2005 | Sun et al. |
| 6,881,192 B1 | 4/2005 | Park |
| 6,904,320 B2 | 6/2005 | Park et al. |
| 6,928,324 B2 | 8/2005 | Park et al. |
| 6,988,498 B2 | 1/2006 | Berthon-Jones et al. |
| 7,016,730 B2 | 3/2006 | Ternes |
| 7,092,755 B2 | 8/2006 | Florio |
| 7,155,278 B2 | 12/2006 | King et al. |
| 7,215,890 B2 | 5/2007 | Tegge, Jr. et al. |
| 7,260,432 B2 | 8/2007 | Kramer et al. |
| 7,519,425 B2 | 4/2009 | Benser et al. |
| 2001/0031930 A1 | 10/2001 | Roizen et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0085741 A1 | 7/2002 | Shimizu |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0120311 A1 | 8/2002 | Lindh et al. |
| 2002/0136328 A1 | 9/2002 | Shimizu |
| 2002/0143264 A1 | 10/2002 | Ding et al. |
| 2002/0193697 A1 | 12/2002 | Cho et al. |
| 2002/0193839 A1 | 12/2002 | Cho et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0023184 A1 | 1/2003 | Pitts-Crick et al. |
| 2003/0036778 A1 | 2/2003 | Ostroff et al. |
| 2003/0045904 A1 | 3/2003 | Bardy et al. |
| 2003/0055461 A1 | 3/2003 | Girouard et al. |
| 2003/0069609 A1 | 4/2003 | Thompson |
| 2003/0083587 A1 | 5/2003 | Ferek-Petric |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0100925 A1 | 5/2003 | Pape et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0187336 A1 | 10/2003 | Odagiri et al. |
| 2003/0195571 A1 | 10/2003 | Burnes et al. |
| 2003/0199945 A1 | 10/2003 | Ciulla |
| 2003/0204146 A1 | 10/2003 | Carlson |
| 2003/0204213 A1 | 10/2003 | Jensen et al. |
| 2003/0212436 A1 | 11/2003 | Brown |
| 2003/0216789 A1 | 11/2003 | Deem et al. |
| 2004/0002742 A1 | 1/2004 | Florio |
| 2004/0030362 A1 | 2/2004 | Hill et al. |
| 2004/0088027 A1 | 5/2004 | Cho et al. |
| 2004/0102814 A1 | 5/2004 | Sorensen et al. |
| 2004/0111021 A1 | 6/2004 | Olson |
| 2004/0111040 A1 | 6/2004 | Ni et al. |
| 2004/0138719 A1 | 7/2004 | Cho et al. |
| 2004/0176809 A1 | 9/2004 | Cho et al. |
| 2004/0210155 A1 | 10/2004 | Takemura et al. |
| 2004/0230230 A1 | 11/2004 | Lindstrom et al. |
| 2004/0230243 A1 | 11/2004 | Haefner et al. |
| 2004/0243012 A1 | 12/2004 | Ciaccio et al. |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0069322 A1 | 3/2005 | Tegge, Jr. et al. |
| 2005/0137632 A1 | 6/2005 | Ding et al. |
| 2007/0118180 A1 | 5/2007 | Ni et al. |
| 2007/0161873 A1 | 7/2007 | Ni et al. |
| 2007/0282215 A1 | 12/2007 | Ni et al. |

FOREIGN PATENT DOCUMENTS

| | | |
|---|---|---|
| EP | 1038498 A2 | 9/2000 |
| EP | 1162125 A2 | 12/2001 |
| EP | 1172125 A1 | 1/2002 |
| EP | 1151718 A3 | 9/2002 |
| EP | 1317943 A1 | 6/2003 |
| EP | 0750920 B1 | 12/2003 |
| WO | WO-8402080 A1 | 6/1984 |
| WO | WO-9203983 A1 | 3/1992 |
| WO | WO-1992017240 A1 | 10/1992 |
| WO | WO-92020402 A1 | 11/1992 |
| WO | WO-9904841 A1 | 2/1999 |
| WO | WO-0001438 A1 | 1/2000 |

(56) References Cited

FOREIGN PATENT DOCUMENTS

WO WO-02087696 A1 11/2002
WO WO-03003905 A2 1/2003

OTHER PUBLICATIONS

"U.S. Appl. No. 11/282,963, Advisory Action dated Feb. 3, 2010", 3 pgs.
"U.S. Appl. No. 11/282,963, Advisory Action dated May 16, 2012", 3 pgs.
"U.S. Appl. No. 11/282,963, Appeal Brief filed Oct. 23, 2012", 22 pgs.
"U.S. Appl. No. 11/282,963, Appeal Decision dated Feb. 17, 2016", 8 pgs.
"U.S. Appl. No. 11/282,963, Decision on Pre-Appeal Brief dated Sep. 13, 2012", 3 pgs.
"U.S. Appl. No. 11/282,963, Examiner Interview Summary dated Mar. 19, 2009", 2 pgs.
"U.S. Appl. No. 11/282,963, Examiner Interview Summary dated Jul. 2, 2010", 3 pgs.
"U.S. Appl. No. 11/282,963, Examiner's Answer dated Dec. 11, 2012", 16 pgs.
"U.S. Appl. No. 11/282,963, Final Office Action dated Mar. 7, 2012", 12 pgs.
"U.S. Appl. No. 11/282,963, Final Office Action dated Nov. 15, 2010", 11 pgs.
"U.S. Appl. No. 11/282,963, Final Office Action dated Nov. 17, 2009", 11 pgs.
"U.S. Appl. No. 11/282,963, Final Office Action dated Nov. 20, 2008", 10 pgs.
"U.S. Appl. No. 11/282,963, Non Final Office Action dated Jan. 29, 2009", 8 pgs.
"U.S. Appl. No. 11/282,963, Non Final Office Action dated Mar. 27, 2008", 11 pgs.
"U.S. Appl. No. 11/282,963, Non Final Office Action dated Mar. 30, 2010", 9 pgs.
"U.S. Appl. No. 11/282,963, Non Final Office Action dated Oct. 5, 2011", 11 pgs.
"U.S. Appl. No. 11/282,963, Notice of Allowance dated May 13, 2016", 7 pgs.
"U.S. Appl. No. 11/282,963, Pre-Appeal Brief Request filed Jun. 28, 2012", 5 pgs.
"U.S. Appl. No. 11/282,963, Reply Brief filed Jan. 25, 2013", 12 pgs.
"U.S. Appl. No. 11/282,963, Response filed Jan. 14, 2010 to Final Office Action dated Sep. 17, 2009", 13 pgs.
"U.S. Appl. No. 11/282,963, Response filed Jan. 21, 2009 to Final Office Action dated Nov. 20, 2008", 13 pgs.
"U.S. Appl. No. 11/282,963, Response filed Feb. 2, 2012 to Non Final Office Action dated Oct. 5, 2011", 15 pgs.
"U.S. Appl. No. 11/282,963, Response filed Mar. 17, 2010 to Advisory Action dated Feb. 3, 2010", 10 pgs.
"U.S. Appl. No. 11/282,963, Response filed Apr. 24, 2012 to Final Office Action dated Mar. 7, 2012", 13 pgs.
"U.S. Appl. No. 11/282,963, Response filed Jul. 20, 2011 to Final Office Action dated Nov. 15, 2015-10", 10 pgs.
"U.S. Appl. No. 11/282,963, Response filed Jul. 27, 2009 to Non Final Office Action dated Jan. 29, 2009", 11 pgs.
"U.S. Appl. No. 11/282,963, Response filed Jul. 31, 2008 to Non Final Office Action dated Mar. 27, 2008", 11 pgs.
"U.S. Appl. No. 11/282,963, Response filed Sep. 21, 2010 to Non Final Office Action dated Mar. 30, 2010", 10 pgs.
Balaban, K. W, et al., "Feasibility of Screening for Sleep Apnea using Pacemaker Impedence Sensor", PACE, vol. 24, Part II, No. 313, (Apr. 2001), p. 313.
Belouchrani, Adel, et al., "Blind Source Separation Based on Time-Frequency Signal Representations", IEEE Transactions on Signal Processing, vol. 46, No. 11, (Nov. 1998), 2888-2897.
Bradley, T . Douglas, et al., "Sleep Apnea and Heart Failure, Part I: Obstructive Sleep Apnea", Special Review, Circulation, vol. 107, (2003), 1671-1678.
Bradley, T. D, et al., "Pathophysiologic and therapeutic implications of sleep apnea in congestive heart failure", J Card Fail., 2(3), (Sep. 1996), 223-40.
Bradley, T. Douglas, et al., "Sleep Apnea and Heart Failure, Part II: Central Sleep Apnea", Special Review, Circulation, vol. 107, (2003), 1822-1826.
Comon, Pierre, "Independent Component Analysis, A New Concept?", Signal Processing, vol. 36, No. 3, (Apr. 1994), 287-314.
Gallois, Philippe, et al., "Multi-Channel Analysis of the EEG Signals and Statistic Particularities for Epileptic Seizure Forecast", Second Joint EMBS/BMES Conference, (Oct. 2002), 208-215.
Garrigue, et al., "Night Atrial Overdrive with DDD Pacing: A New Therapy for Sleep Apnea Syndrome", Hospital Cardiologique du Haut-Leveque, University of Bordeaux, Pessac-Bordeaux, France, (2000), 591.
Garrigue, S., et al., "Benefit of Atrial Pacing in Sleep Apnea Syndrome", The New England Journal of Medicinem 346(6), (2002), 404-412.
Garrigue, S., et al., "Night Atrial Overdrive with DOD Pacing Results in a Significant Reduction of Sleep Apnea Episodes and QOL Improvement in Heart Failure Patients", (Abstract No. 145), NASPE Abstracts, Abstract Session 25: Bradycardia III: Pacing in Clinical Practice, PACE, vol. 24, Part II, (Apr. 2001), p. 575.
Gradaus, Rainer, et al., "Nonthoracotomy Implantable Cardioverter Defibrillator Placement in Children: Use of Subcutaneous Array Leads and Abdominally Placed Implantable Cardioverter Defibrillators in Children", Journal of Cardiovascular Electrophysiology, 12(3), (Mar. 2001), 356-360.
Hartz, Renee, et al., "New Approach to Defibrillator Insertion", J. Thoracic Cardiovascular Surgery, vol. 97, (1989), 920-922.
Hilton, et al., "Evaluation of Frequency and Time-frequency Spectral Analysis of Heart Rate Variability as a Diagnostic Marker of the Sleep Apnea Syndrome", Med Biol Eng Comput, 37(6), (Nov. 1999), 760-69.
Hyvarinen, A, et al., "Independent Component Analysis: A Tutorial", Helsinski Univ. of Technology, (Apr. 1999).
Javaheri, et al., "Sleep Apnea in 81 Ambulatory Male Patients with Stable Heart Failure—Types and Their Prevalences, Consquences, and Presentations", Circulation, 97, (1998), 2154-2159.
Kaneko, Y., et al., "Cardiovascular effects of continuous positive airway pressure in patients with heart failure and obstructive sleep apnea.", N Engl J Med., 348(13), (Mar. 27, 2003), 1233-41.
Kolettis, Theofilos M, et al., "Submammary Implantation of a Cardioverter-Defibrillator with a Nonthoractomy Lead System", Am. Heart J., vol. 126, (Nov. 1993), 1222-1223.
Krahn, A. D, et al., "Recurrent Syncope. Experience with an Implantable Loop Record", Cardiol. Clin., vol. 15, No. 2, (May 1997), 316-326.
Leng, Charles T, et al., "Lead Configuration for Defibrillator Implantation in a Patient with Congenital Heart Disease and a Mechanical Prosthetic Tricuspid Valve", PACE, 24(8), (Aug. 2001), 1291-1292.
Mettauer, B., et al., "VO2 kinetics reveal a central limitation at the onset of subthreshold exercise in heart transplant recipients", J Applied Physiology 88, (2000), 1228-1238.
Olusola, et al., "Nightcap: Laboratory and home-based evaluation of a portable sleep monitor", Psychophysiology, 32, Abstract only, (1995), 32-98.
Park, et al., "Use of an Implantable Cardioverter Defibrillator in an Eight-Month-Old Infant with Ventricular Fibrillation Arising from a Myocardial Fibroma", PACE, 22(1), (Jan. 1999), 138-139.
Rieta, J. J, et al., "Atrial Activity Extraction Based on Blind Source Separation as an Alternative to QRST Cancellation for Atrial Fibrillation Analysis", Computers in Cardiology, vol. 27, (2000), 69-72.
Roche, et al., "Screening of Obstructive Sleep Apnea Syndrome by Heart Rate Variability Analysis", Circulation, 100(13), (Sep. 28, 1999), 1411-1455.

(56) References Cited

OTHER PUBLICATIONS

Schuder, John C, et al., "Experimental Ventricular Defibrillation with an Automatic and Completely Implanted System", Trans. Am. Soc. Artif. Int. Organs, vol. 16, (1970), 207-212.

Schuder, John C, et al., "Transthoracic Ventricular Defibrillation in the Dog with Truncated and Untruncated Exponential Stimuli", IEEE Trans. on Bio-Medical Engin., vol. BME-18, No. 6, (Nov. 1971), 410-415.

Schuder, John C, et al., "Ventricular Defibrillation in the Dog using Implanted and Partially Implanted Electrode Systems", Am. J. of Cardiology, vol. 33, (Feb. 1974), 243-247.

Shahrokh, "A Mechanism of Central Sleep Apnea in Patients with Heart Failure", New England Journal of Medicine, 341(13), (Sep. 1999), 949-954.

Smits, et al., "Defibrillation Threshold (DFT) Model of a Fully Subcutaneous ICD System", Eurospace Supplements, vol. 2, (Jun. 2001), B83.

Stirbis, et al., "Optmizing the Shape of Implanted Artificial Pacemakers", Kaunas Medical Institute. Translated from Meditsinskaya Tekhnika, No. 6, (1986), 25-27.

Tkacova, Niroumand R, et al., "Overnight shift from obstructive to central apneas in patients with hearl failure", Role of PCO2 in circulatory delay. Circulation, vol. 103, (2001), 238-243.

Vanninen, et al., "Cardiac Sympathovagal Balance During Sleep Apnea Episodes", Cliln Physiol, 16(3), (May 1996), 209-16.

Verrier, et al., "Sleep Related Cardiovascular Risk: New Home-Based Monitoring Technology for Improved Diagnosis and Therapy", A.N.E., 2, (1997), 158-175.

Verrier, et al., "Sleep, dreams, and sudden death: the case for sleep as an autonomic stress test for the heart", Cardiovascular Research, 31, (1996), 181-211.

Waldemark, "Detection of Apnea Using Short Window FFT Technique and Artificial Neural Network", SPIE, International Society for Optical Engineering, vol. 3390, (1998), 122-133.

Young, Terry, et al., "The Occurrence of Sleep-disordered Breathing Among Middle-aged Adults", The New England Journal of Medicine, 328(17), (1993), 1230-1235.

Zarzoso, Vicente, et al., "Blind Separation of Independent Sources for Virtually Any Probability Density Function", IEEE Transactions on Signal Processing, vol. 47, No. 9, (Sep. 1999), 2419-2432.

Zarzoso, Vicente, et al., "Noninvasive Fetal Electrocardiogram Extraction: Blind Separation Versus Adaptive Noise Cancellation", IEEE Transactions on Biomedical Engineering, vol. 48, No. 1, (Jan. 2001), 12-18.

CARDIAC RESYNCHRONIZATION THERAPY FOR IMPROVED HEMODYNAMICS BASED ON DISORDERED BREATHING DETECTION

CLAIM OF PRIORITY

This application is a continuation of U.S. application Ser. No. 11/282,963, filed Nov. 18, 2005, now abandoned, which is herein incorporated by reference in its entirety.

FIELD OF THE INVENTION

The present invention relates generally to implantable medical devices and, more particularly, to cardiac sensing and/or stimulation devices with disordered breathing detection.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias, as well as for patients with conditions such as heart failure. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

People with severe cardiopulmonary deficiencies, such as those associated with chronic heart failure and other cardiopulmonary maladies, are particularly susceptible to morbidities associated with disordered breathing conditions such as sleep apnea. Disordered breathing may be caused by a wide spectrum of respiratory conditions involving the disruption of the normal respiratory cycle. Although disordered breathing often occurs during sleep, the condition may also occur while the patient is awake. Respiratory disruption can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, orthopnea, paroxysmal nocturnal dyspnea, and periodic breathing, including Cheyne-Stokes respiration (CSR). Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

SUMMARY OF THE INVENTION

The present invention is directed to methods and devices that detect the presence of disordered breathing and a cardiac condition indicative of a patient's cardiac status. Methods and devices of the present invention are further directed to identifying a patient as suitable for a cardiac resynchronization therapy based on the presence of disordered breathing and a cardiac condition indicative of a patient's cardiac status.

According to embodiments of the present invention, the presence of disordered breathing is detected using an implantable medical device. A cardiac condition is detected that is indicative of the patient's cardiac status. Based on the presence of disordered breathing and the cardiac condition, the patient is identified as suitable for a cardiac resynchronization therapy.

Such methods may further involve delivering at least one of a cardiac pacing therapy other than a cardiac resynchronization therapy, a cardiac shock therapy, and a cardiac neurostimulation therapy. Detecting the presence of disordered breathing may involve detecting at least one of obstructive sleep apnea, central sleep apnea, hypopnea, orthopnea, paroxysmal nocturnal dyspnea, and Cheyne-Stokes respiration.

The implantable medical device may be enabled to perform the cardiac resynchronization therapy based on identifying the patient as suitable for the cardiac resynchronization therapy. For example, a pulse generator may be provided in the implantable medical device and coupled to electrodes, and the pulse generator and electrodes may be configured for cardiac resynchronization therapy delivery. One or more of initiating, terminating, adjusting, or optimizing the cardiac resynchronization therapy may be effected in response to detecting the presence of disordered breathing and the cardiac condition.

Detecting the cardiac condition may involve detecting a ventricular dysynchrony in the patient's heart via an implantable or patient-external sensing arrangement. Detecting the cardiac condition may also involve detecting left ventricular systolic dysfunction via an implantable or patient-external sensing arrangement. Detecting the cardiac condition may further involve detecting a left ventricular systolic dysfunction comprising a left ventricular ejection fraction value less than a predetermined limit. Detecting the cardiac condition may involve determining that a QRS complex pulse width of a cardiac cycle exceeds a predetermined limit. Detecting the cardiac condition may also involve detecting a ventricular wall motion asynchrony that exceeds a predetermined limit.

Detecting the presence of disordered breathing may be used to trigger an alert using a patient-external device or a transfer of data from the implantable medical device to the patient-external device. Detecting the presence of disordered breathing may involve detecting an apnea/hypopnea index greater than a predetermined limit. According to one approach, the implantable medical device may be enabled to perform a first cardiac resynchronization therapy in response to detecting obstructive sleep apnea, and enabled to perform a second cardiac resynchronization therapy after detecting central sleep apnea.

In embodiments that incorporate a pulse generator, methods of the present invention provide for adjusting an atrioventricular delay based on the detected disordered breathing. The cardiac resynchronization therapy, in such embodiments, may involve selecting a cardiac stimulation vector based on the detected disordered breathing.

In accordance with other embodiments, an implantable medical device included a housing configured for implantation in a patient. A lead system comprises an electrode arrangement and is coupled to the housing. A processor is provided in the housing and coupled to the lead system. The processor is configured to detect presence of disordered breathing, detect a cardiac condition indicative of the patient's cardiac status, and identify the patient as suitable for a cardiac resynchronization therapy based on the presence of disordered breathing and the cardiac condition.

The implantable medical device may include a pulse generator coupled to the processor and configured to deliver at least one of a cardiac pacing therapy other than a cardiac resynchronization therapy, a cardiac shock therapy, and a cardiac neurostimulation therapy. The processor may be configured to enable the pulse generator to perform the cardiac resynchronization therapy based on identifying the patient as suitable for the cardiac resynchronization therapy. The processor may be configured to adjust an atrioventricular delay based on the detected disordered breathing. The processor may be configured to detect at least one of obstructive sleep apnea, central sleep apnea, hypopnea, orthopnea, paroxysmal nocturnal dyspnea, and Cheyne-Stokes respiration.

In other embodiments, one or both of an implantable sensor arrangement and a patient-external sensor arrangement may be coupled to the implantable medical device. The processor may be configured to detect a ventricular dysynchrony in the patient's heart via one or both of the implantable or patient-external sensing arrangement. The processor may be coupled to communication circuitry configured to facilitate wireless communication between the processor and a patient-external device or system. The patient-external device or system may be configured to generate a clinician alert to initiate, terminate, adjust, or optimize the cardiac resynchronization therapy. The implantable medical device may include a transthoracic impedance measuring circuitry coupled to the processor and configured to detect patient breathing.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
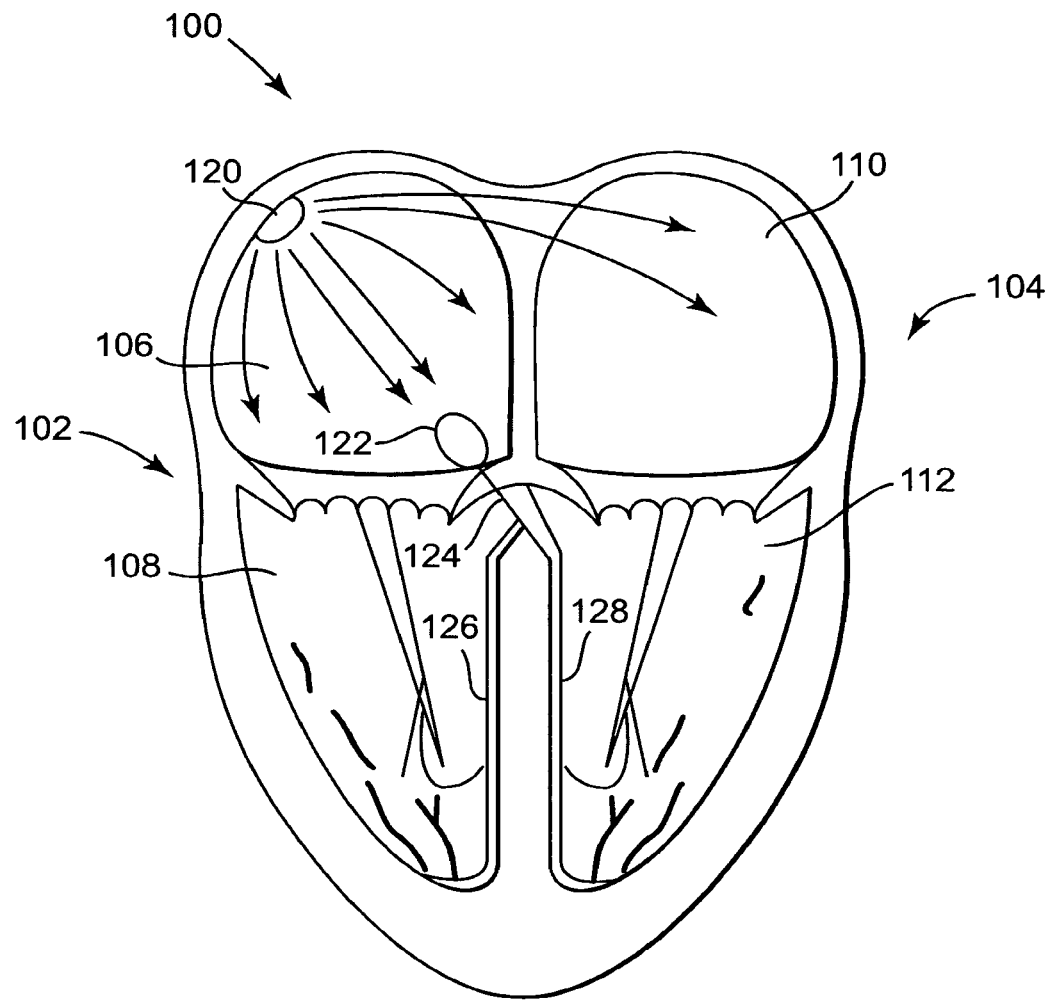
FIG. 1 is a sectional view of a heart illustrating the chambers and electrical conduction pathways.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a monitoring device, diagnostic device, or a stimulation device (e.g., cardiac stimulator or cardiac neurostimulation device) may be implemented to include one or more of the advantageous features and/or processes described below. It is intended that such a monitor, diagnostic device, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable monitoring and/or stimulation devices may be configured to implement methodologies of the present invention, including cardiac monitoring or pacing devices, cardiac defibrillation devices, cardiac neurostimulation devices, cardio-respiratory detection of therapy devices, and other implantable devices that provide for monitoring of physiological signals of a patient. Such devices may include, for example, cardiac resynchronization therapy for improved hemodynamics based on disordered breathing detection in accordance with the present invention. Other non-limiting, representative examples of cardiac devices includes cardiac monitors, pacemakers, cardioverters, defibrillators, resynchronizers, and other cardiac monitoring and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of medical devices, such as those listed above, and are referred to herein generally as patient-internal medical devices (PIMD) for convenience. A PIMD implemented in accordance with the present invention may incorporate one or more of the electrode types identified above and/or combinations thereof.

The following description is directed generally to aspects of the invention embodied in various types of implantable cardiac devices. It is understood that aspects of the invention may be implemented in other types of implantable medical devices, such as cardio-respiratory monitoring devices, cardiac neurostimulation devices, and other monitoring, diagnostic, or stimulation devices, as for example.

The heart is a muscular organ comprising multiple chambers that operate in concert to circulate blood throughout the body's circulatory system. As shown in FIG. 1, a heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries (not shown). Within the lungs, waste products (e.g., carbon dioxide) are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. When the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase (e.g., systole), the ventricular muscle cells of the right and left ventricles 108, 112 contract to pump blood through the pulmonary circulation and throughout the body, respectively. Conversely, during the diastolic phase (e.g., diastole), the ventricular muscle cells of the right and left ventricles 108, 112 relax, during which the right and left atriums 106, 110 contract to force blood into the right and left ventricles 108, 112, respectively. Typically, the cardiac cycle occurs at a frequency between 60 and 100 cycles per minute and can vary depending on physical exertion and/or emotional stimuli, such as, pain or anger. The volume of blood pumped from the left ventricle (expressed as a percentage), relative to the total volume of blood in the left ventricle before contraction, is known as the left ventricular ejection fraction (LVEF).

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 1, the complex conduction system includes an atrial node 120 (e.g., the sinoatrial node) and a ventricular node 122 (e.g., the atrioventricular node). The sinoatrial node 120 initiates an electrical impulse that spreads through the muscle tissues of the right and left atriums 106, 110 and the atrioventricular node 122. As a result, the right and left atriums 106, 110 contract to pump blood into the right and left ventricles 108, 112 as discussed above. At the atrioventricular node 122, the electrical signal is momentarily delayed before propagating through the right and left ventricles 108, 112. Within the right and left ventricles 108, 112, the ventricular conduction system includes right and left bundles branches 126, 128 that extend from the atrioventricular node 122 via a Bundle of His 124. The electrical impulse spreads through the muscle tissues of the right and left ventricles 108, 112 via the right and left bundle branches 126, 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106, 110 contract (e.g., atrial contractions) and relax synchronously. Shortly after the atrial contractions, both the right and left ventricles 108, 112 contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular relations and filling. In situations where the blockage is in the ventricles (e.g., the right and left bundle branches 126, 128), the right and/or left ventricles 108, 112 can only be excited through slow muscle tissue conduction. As a result, the muscular walls of the affected ventricle (108 and/or 112) do not contract synchronously (e.g., asynchronous contraction), thereby, reducing the overall effectiveness of the heart 100 to pump oxygen-rich blood throughout the body. For example, asynchronous contraction of the left ventricular muscles can degrade the global contractility (e.g., the pumping power) of the left ventricle 112 which can be measured by the peak ventricular pressure change during systole (denoted as "LV+dp/dt"). A decrease in LV+dp/dt corresponds to a worsened pumping efficiency.

Similarly, heart valve disorders (e.g., valve regurgitation or valve stenosis) can interfere with the heart's 100 ability to pump blood, thereby, reducing stroke volume (i.e., aortic pulse pressure) and/or cardiac output.

Various medical procedures have been developed to address these and other heart disorders. In particular, cardiac resynchronization therapy can be used to improve the conduction pattern and sequence of the heart. CRT involves the use of an artificial electrical stimulator that is surgically implanted within the patient's body. Leads from the stimulator can be affixed at a desired location within the heart to effectuate synchronous atrial and/or ventricular contractions. Typically, the location of the leads (e.g., stimulation site) is selected based upon the severity and/or location of the blockage. Electrical stimulation signals can be delivered to resynchronize the heart, thereby, improving cardiac performance.

Results from clinical studies have shown that hemodynamic response to CRT typically varies from patient to patient, ranging from very positive (e.g., improvement) to substantially negative (e.g., deterioration). Additionally, hemodynamic response can also vary based upon the stimulation site used to apply CRT. CRT therapy is currently not indicated for patients with mild symptoms of heart failure, due to the potential for a negative hemodynamic response as seen in the above mentioned clinical study results.

Sleep disordered breathing (SDB), including obstructive and central sleep apneas and hypopneas, can cause pathophysiological changes that directly relate to progression of heart failure. Mechanical therapy for obstructive sleep apnea (OSA) has shown benefits in reduced daytime systolic hypertension, mean heart rate, left-ventricular end-systolic dimensions, and improved LVEF. This suggests a cause-effect relationship between OSA and CHF. Patients with early stage CHF and OSA are likely to have a worse clinical trajectory than patients without SDB.

CSA, unlike OSA, can arise as a consequence of heart failure. CSA associated with CSR may be considered as a reflection of severely compromised cardiac function with elevated left-ventricular filling pressure. CSA may also reflect acute changes of left-ventricular function. Overnight deterioration of cardiac function related to OSA in the early part of sleep may cause a shift to CSA in the later part of sleep. Thus, CSA during sleep may provide an early indication of impaired left-ventricular function before the impairment is reflected in general functional status, such as assessed by New York Heart Association (NYHA) functional class.

Methods and devices in accordance with the present invention identify a subset of patients who are likely positive responders to CRT. In patients qualified according to embodiments of the present invention, the presence of sleep disordered breathing is used to invoke and/or perform one or more of the following actions: 1) Identify cardiac rhythm management (CRM) patients likely to benefit from CRT; 2) Enable CRT using a CRM system already implanted in a patient; 3) Improve a CRT therapy using an SDB index; 4) Display and/or provide information of a patient's SDB presence and/or severity to a clinician; 5) Adjust a CRM device's parameters based on a measured severity of SDB; and 6) Adjust a CRM device's parameters based on a detected presence and/or a measured severity of one or more of OSA, Central sleep apnea (CSA), orthopnea, paroxysmal nocturnal dyspnea, and Cheyne-Stokes respiration (CSR). Providing and/or adjusting CRT therapy in qualified patients may reduce cardiac dyssynchrony, improve cardiac function, reduce SDB, and/or improve the prognosis of heart failure patients.

The subset of CHF patients that may benefit from CRT may be qualified by one or more of the following measurements in combination with sleep disordered breathing detection of CSA, CSR and/or an apnea/hypopnea index (AHI) value or other useful disordered breathing index value greater than a predetermined limit, such as about 15 episodes per hour. Qualifying measurements include: an LVEF less than a predetermined limit (e.g., about 0.4), ventricular dysynchrony (which may be detected via implantable or patient-external sensors) beyond a predetermined threshold or limit, such as a QRS complex width greater than a predetermined threshold, such as about 120 milliseconds, left ventricular dysfunction detected via implantable or patient-external sensors, ventricular wall motion asynchrony that exceeds a predetermined limit (such as is described in commonly owned US Patent Publication 2004/0015081, which is hereby incorporated herein by reference), and an NYHA functional classification of III or IV.

Figure 2:
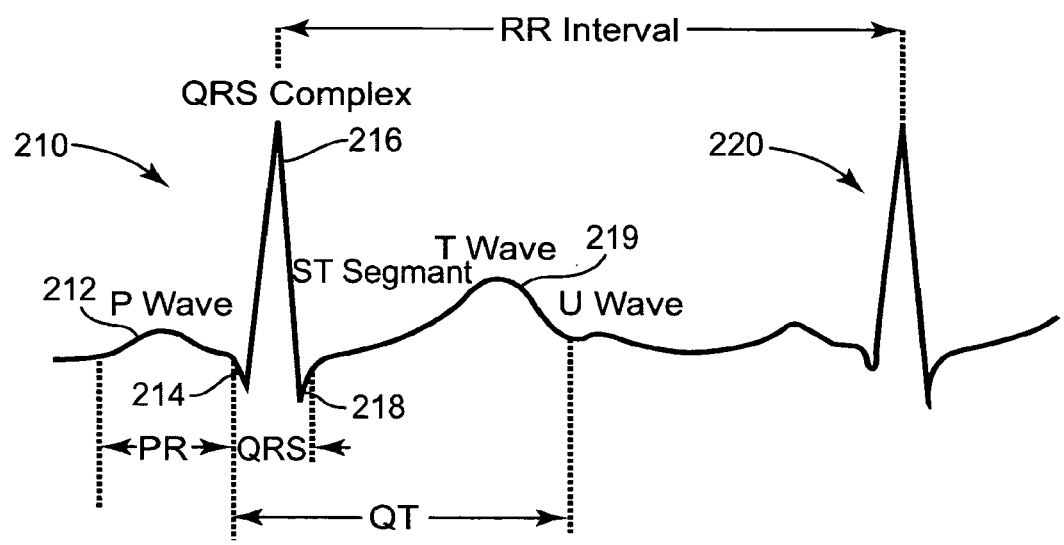
FIG. 2 is a pictorial diagram of an electrocardiogram (ECG) waveform for two consecutive heartbeats.

As an example, a device or method in accordance with the present invention may qualify a patient for CRT using a cardiac dyssynchrony measurement as obtained by the QRS complex width, and a detection and measurement of an AHI index value. Referring to FIG. 2, an ECG waveform 200 describes the activation sequence of a patient's heart as recorded, for example, by a bi-polar cardiac sensing electrode of such a device. FIG. 2 is a magnified view of a first heartbeat 210 and a second heartbeat 220 of a patient's ECG waveform.

Referring to the first heartbeat 210, the portion of the ECG waveform representing depolarization of the atrial muscle fibers is referred to as a P-wave 212. Depolarization of the ventricular muscle fibers is collectively represented by a Q 214, R 216, and S 218 waves of the ECG waveform 200, typically referred to as the QRS complex, which is a well-known morphologic feature of electrocardiograms. Finally, the portion of the waveform representing repolarization of the ventricular muscle fibers is known as a T wave 219. Between contractions, the ECG waveform returns to an isopotential level.

The sensed ECG waveform 200 illustrated in FIG. 2 is typical of a far-field ECG signal, effectively a superposition of all the depolarizations occurring within the heart that result in contraction. The ECG waveform 200 may also be obtained indirectly, such as by using a signal separation methodology. Signal separation methodologies, such as blind source separation (BSS), are able to separate signals from individual sources that are mixed together into a composite signal. Signal separation techniques may be used to determine ventricular dyssynchrony, such as is further described in commonly owned U.S. patent application Ser. No. 10/955,397 filed on Sep. 30, 2004, which is hereby incorporated herein by reference.

For purposes of illustration, and not of limitation, various embodiments of devices that may be used to identify a patient as suitable for cardiac resynchronization therapy based on disordered breathing detection in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for monitoring physiological signals and, if so configured, delivering a therapy to the patient. For example, the PIMD may be configured to provide for monitoring of cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and/or deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. patent application Ser. No. 10/465,520 filed Jun. 19, 2003, entitled "Methods and Systems Involving Subcutaneous Electrode Positioning Relative to a Heart"; Ser. No. 10/795,126 filed Mar. 5, 2004, entitled "Wireless ECG In Implantable Devices"; and Ser. No. 10/738,608 filed Dec. 17, 2003, entitled "Noise Canceling Cardiac Electrodes," which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of the present invention are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

Various embodiments described herein may be used in connection with congestive heart failure (CHF) monitoring, diagnosis, and/or therapy. A PIMD of the present invention may incorporate CHF features involving dual-chamber or bi-ventricular pacing therapy, cardiac resynchronization therapy, cardiac function optimization, or other CHF related methodologies. For example, any PIMD of the present invention may incorporate features of one or more of the following references: commonly owned U.S. patent application Ser. No. 10/270,035, filed Oct. 11, 2002, entitled "Timing Cycles for Synchronized Multisite Cardiac Pacing;" and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

Figure 3A:
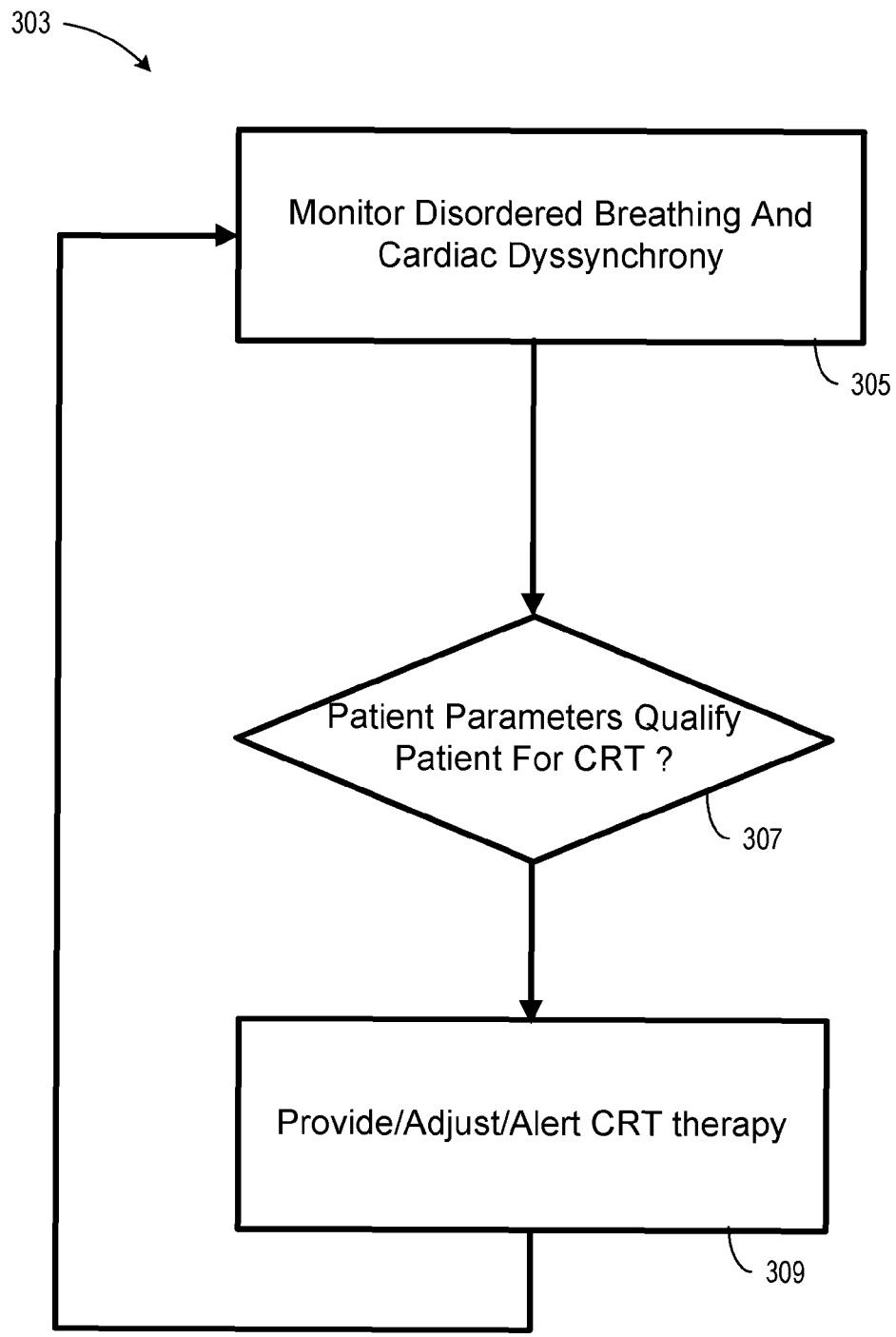
FIG. 3A illustrates an embodiment of a method in accordance with the present invention that qualifies a patient for cardiac resynchronization therapy (CRT) using a cardiac dyssynchrony measurement, and a detection and measurement of an AHI index value.

FIG. 3A illustrates an embodiment of a method 303 in accordance with the present invention that qualifies a patient for CRT using a cardiac dyssynchrony and SDB detection/measurement 305. The cardiac dyssynchrony and SDB detection/measurement 305 may be performed by a single device, such as a PIMD, or may be performed by a PIMD in combination with an external device, such as by using an advanced patient management system, as will be further described below.

The cardiac dyssynchrony and SDB detection/measurement 305 involves a measure of cardiac function, such as LVEF, QRS complex width, or other measure of cardiac function, as well as a measure of SDB, such as an AHI or other measure/detection of OSA, CSA, CSR, or the like. A decision 307 qualifies the patient for CRT, such as by detecting/measuring a combination of a QRS complex width greater than about 120 milliseconds and an apnea/hypopnea index (AHI) value greater than about 15 episodes per hour, for example.

If the patient is qualified by decision 307, then a CRT therapy 309 involves one or more of providing a CRT therapy, adjusting a CRT therapy, and/or alerting a clinician to the qualification of the patient for the CRT therapy. For example, the following actions may be implemented: 1) Identify the cardiac rhythm management (CRM) patient as likely to benefit from CRT; 2) Enable CRT using a CRM system already implanted in the patient; 3) Modify an existing CRT therapy using the AHI value; 4) Display and/or provide information of the patient's SDB presence and/or severity to a clinician; 5) Adjust a CRM device's parameters based on a measured severity of SDB; and 6) Adjust a CRM device's parameters based on a detected presence and/or a measured severity of one or more of OSA, Central sleep apnea (CSA), orthopnea, paroxysmal nocturnal dyspnea, and Cheyne-Stokes respiration (CSR). Providing and/or Adjusting CRT therapy 309 in qualified patients may reduce cardiac dyssynchrony, improve cardiac function, reduce SDB, and improve the prognosis of heart failure patients.

Figure 3B:
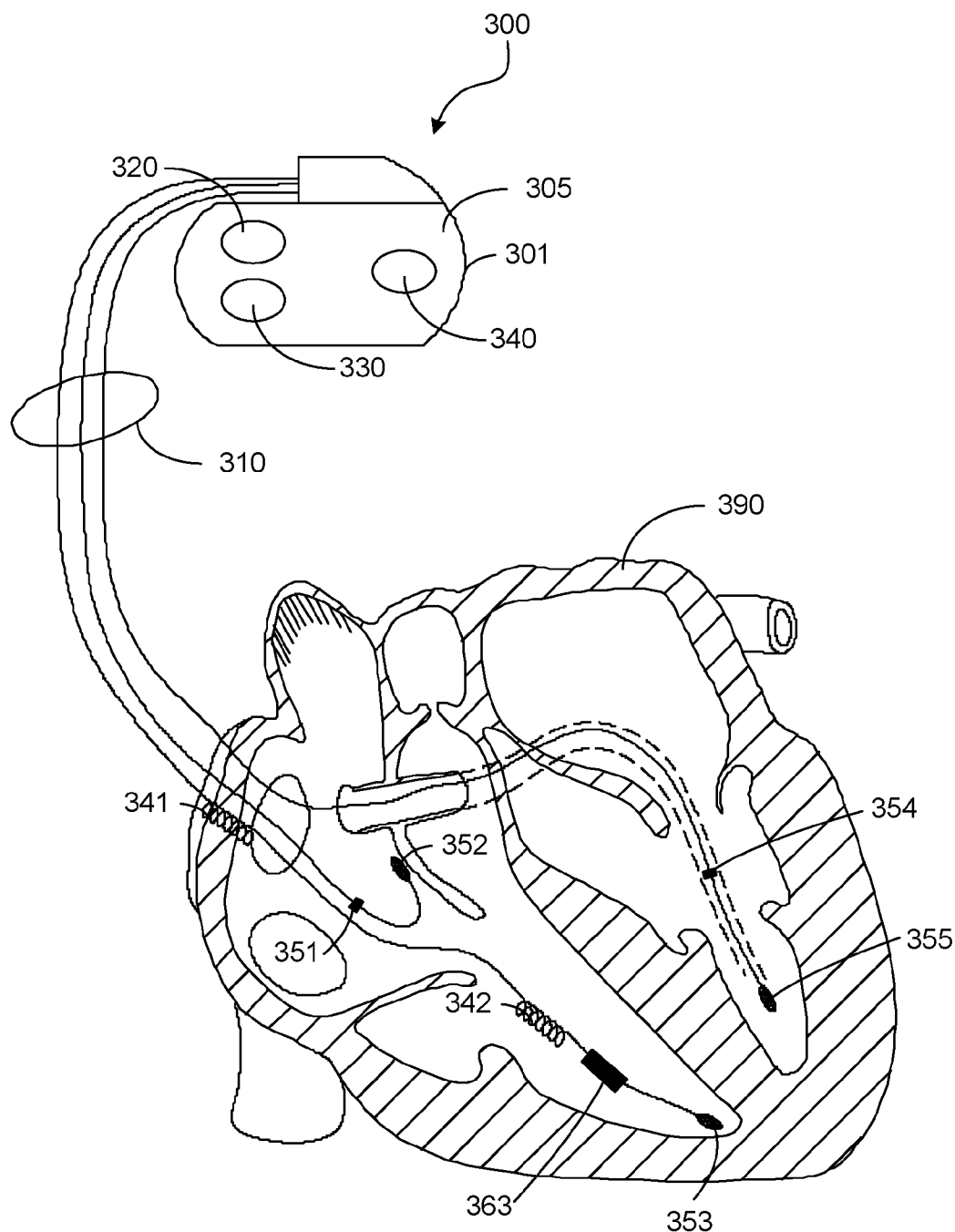
FIG. 3B is an illustration of an implantable cardiac device including a lead assembly shown implanted in a sectional view of a heart, in accordance with embodiments of the invention.

Referring now to FIG. 3B, the implantable device illustrated in FIG. 3B is an embodiment of a PIMD that may incorporate cardiac resynchronization therapy for improved hemodynamics based on disordered breathing detection and ventricular dyssynchrony measurement in accordance with the present invention. In this example, the implantable device includes a cardiac rhythm management device (CRM) 300 including an implantable pulse generator 305 electrically and physically coupled to an intracardiac lead system 310.

Portions of the intracardiac lead system 310 are inserted into the patient's heart 390. The intracardiac lead system 310 includes one or more electrodes configured to sense electrical cardiac activity of the heart, deliver electrical stimulation to the heart, sense the patient's transthoracic impedance, and/or sense other physiological parameters, e.g, cardiac chamber pressure or temperature. Portions of the housing 301 of the pulse generator 305 may optionally serve as a can electrode.

Communications circuitry is disposed within the housing 301 for facilitating communication between the pulse generator 305 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 305 may optionally incorporate a motion detector 320 that may be used to sense patient activity as well as various respiratory and cardiac related conditions. For example, the motion detector 320 may be optionally configured to sense snoring, activity level, and/or chest wall movements associated with respiratory effort, for example. The motion detector 320 may be implemented as an accelerometer positioned in or on the housing 301 of the pulse generator 305. If the motion sensor is implemented as an accelerometer, the motion sensor may also provide respiratory, e.g. rales, coughing, and cardiac, e.g. S1-S4 heart sounds, murmurs, and other acoustic information.

The pulse generator 305 may optionally incorporate a posture detector 340 that may be used to sense patient posture. Posture detection is beneficial in the evaluation of sleep and sleep disordered breathing.

The lead system 310 and pulse generator 305 of the CRM 300 may incorporate one or more transthoracic impedance sensors that may be used to acquire the patient's respiratory waveform, or other respiratory-related information. The transthoracic impedance sensor may include, for example, one or more intracardiac electrodes 341, 342, 351-355, 363 positioned in one or more chambers of the heart 390. The intracardiac electrodes 341, 342, 351-355, 363 may be coupled to impedance drive/sense circuitry 330 positioned within the housing of the pulse generator 305.

In one implementation, impedance drive/sense circuitry 330 generates a current that flows through the tissue between an impedance drive electrode 351 and a can electrode on the housing 301 of the pulse generator 305. The voltage at an impedance sense electrode 352 relative to the can electrode changes as the patient's transthoracic impedance changes. The voltage signal developed between the impedance sense electrode 352 and the can electrode is detected by the impedance sense circuitry 330. Other locations and/or combinations of impedance sense and drive electrodes are also possible.

The lead system 310 may include one or more cardiac pace/sense electrodes 351-355 positioned in, on, or about one or more heart chambers for sensing electrical signals from the patient's heart 390 and/or delivering pacing pulses to the heart 390. The intracardiac sense/pace electrodes 351-355, such as those illustrated in FIG. 3B, may be used to sense and/or pace one or more chambers of the heart, including the left ventricle, the right ventricle, the left atrium and/or the right atrium. The lead system 310 may include one or more defibrillation electrodes 341, 342 for delivering defibrillation/cardioversion shocks to the heart.

The pulse generator 305 may include circuitry for detecting cardiac arrhythmias and/or for controlling pacing or defibrillation therapy in the form of electrical stimulation pulses or shocks delivered to the heart through the lead system 310. The pulse generator 305 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and US Patent Publication No. 2002/0143264, which are hereby incorporated herein by reference.

Figure 4:
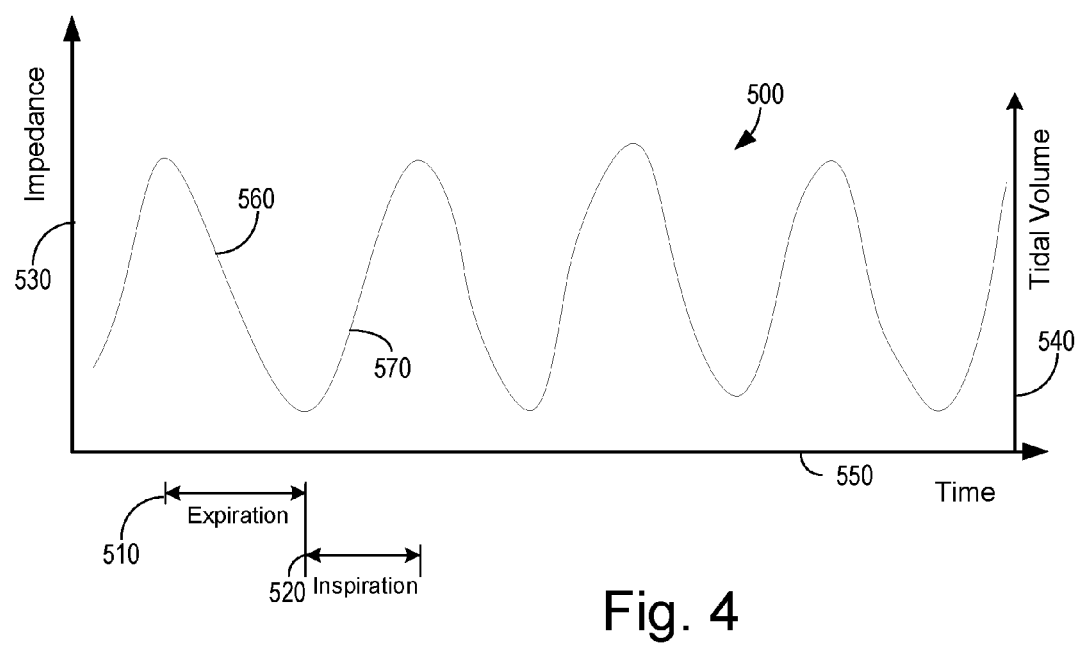
FIG. 4 is a graph of a normal respiration signal measured by a transthoracic impedance sensor that may be utilized for monitoring, diagnosis and/or therapy in accordance with embodiments of the invention.

Referring now to FIG. 4, an impedance signal 500 is illustrated. Transthoracic impedance may be useful for detecting sleep-state and other indirect measurements of brain activity, such as seizures, as well as breathing disorders. The impedance signal 500 may be developed, for example, from an impedance sense electrode in combination with a PIMD device. The impedance signal 500 is proportional to the transthoracic impedance, illustrated as an Impedance 530 on the abscissa of the left side of the graph in FIG. 4.

The impedance 530 increases during any respiratory inspiration 520 and decreases during any respiratory expiration 510. The impedance signal 500 is also proportional to the amount of air inhaled, denoted by a tidal volume 540, illustrated on the abscissa of the right side of the graph in FIG. 4. The variations in impedance during respiration, identifiable as the peak-to-peak variation of the impedance signal 500, may be used to determine the respiration tidal volume 540. Tidal volume 540 corresponds to the volume of air moved in a breath, one cycle of expiration 510 and inspiration 520. A minute ventilation may also be determined, corresponding to the amount of air moved per a minute of time 550 illustrated on the ordinate of the graph in FIG. 4.

The onset of breathing disorders may be determined using the impedance signal 530, and detected breathing disorder information may be used to activate therapy in accordance with the present invention. During non-REM sleep, a normal respiration pattern includes regular, rhythmic inspiration-expiration cycles without substantial interruptions. When the tidal volume of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value for a predetermined time, e.g., equal to or greater than about 10 seconds. If the patient's tidal volume falls further to an apnea threshold, e.g., about 10% of the recent average tidal volume or other baseline value for a predetermined time, e.g., equal to or greater than about 10 seconds, an apnea event is declared.

An adequate quality and quantity of sleep is required to maintain physiological homeostasis. Prolonged sleep deprivation or periods of highly fragmented sleep ultimately has serious health consequences. Chronic lack of sleep may be associated with various cardiac or respiratory disorders affecting a patient's health and quality of life. Methods and systems for collecting and assessing sleep quality data are described in commonly owned U.S. patent application Ser. No. 10/642,998, entitled "Sleep Quality Data Collection and Evaluation," filed on Aug. 18, 2003, and hereby incorporated herein by reference. Evaluation of the patient's sleep patterns and sleep quality may be an important aspect of providing coordinated therapy to the patient, including respiratory and cardiac therapy.

Figure 5:
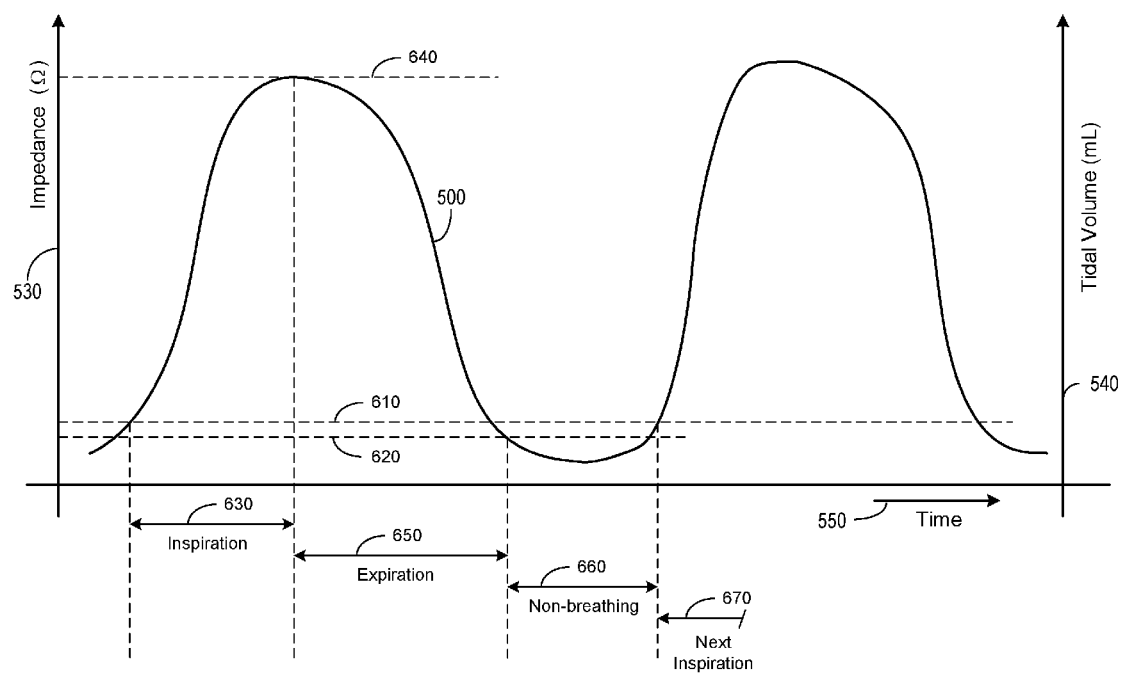
FIG. 5 is a respiration signal graph illustrating respiration intervals used for disordered breathing detection according to embodiments of the invention.
Figure 6:
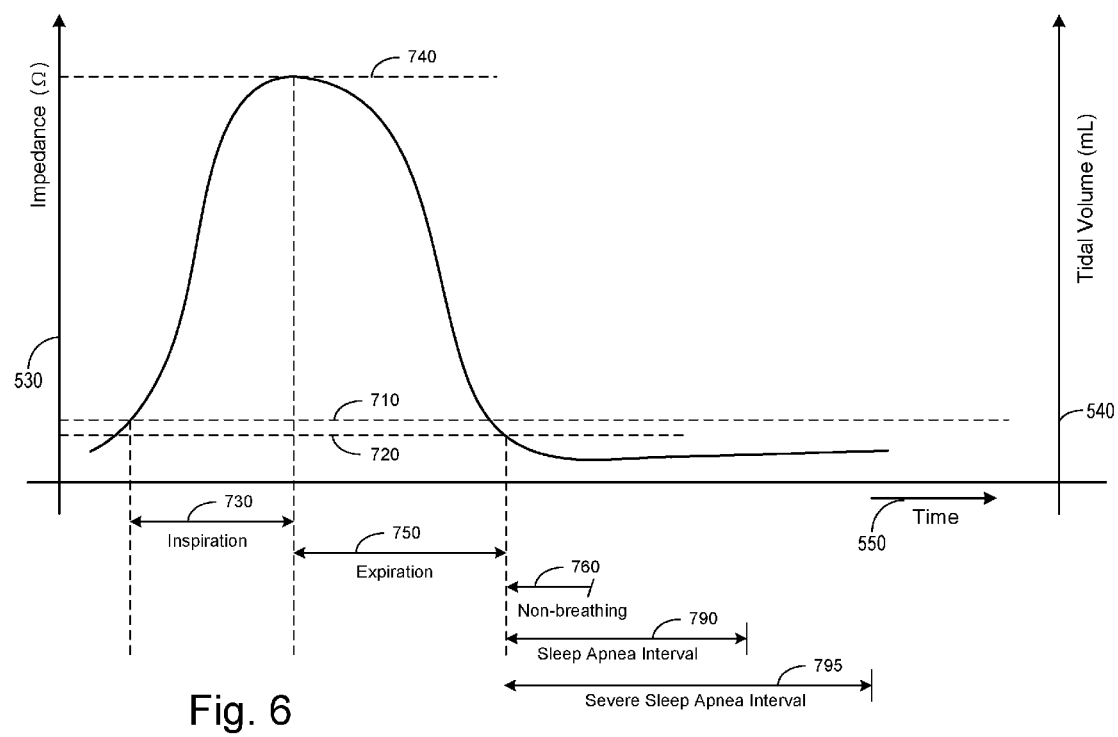
FIG. 6 is a graph of a respiration signal illustrating various intervals that may be used for detection of apnea in accordance with embodiments of the invention.
Figure 7:
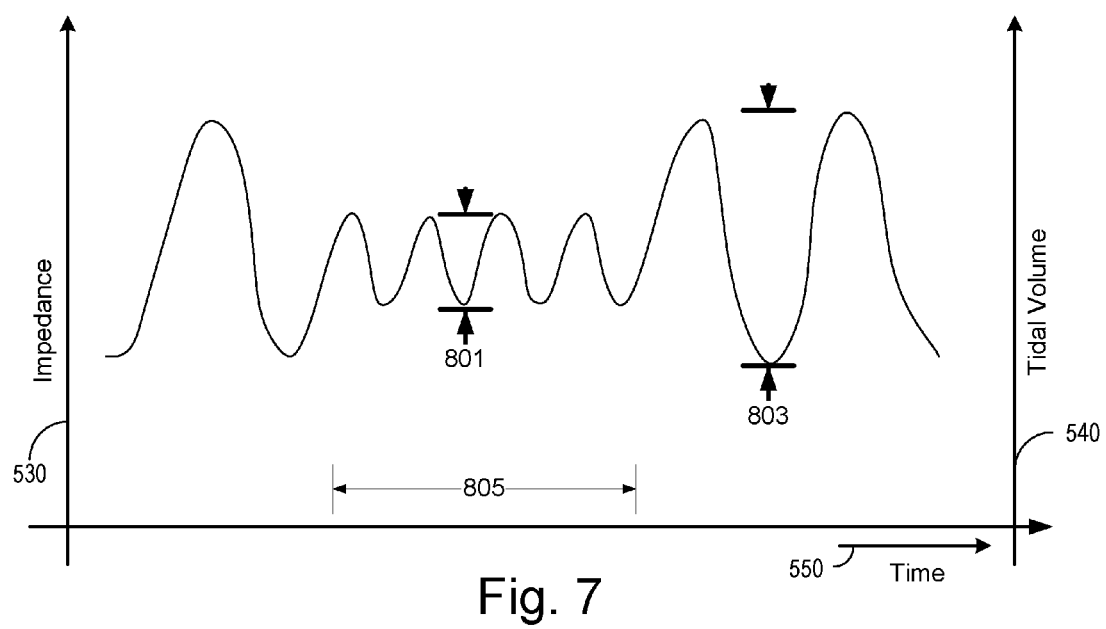
FIG. 7 is a respiration graph illustrating abnormally shallow respiration utilized in detection of disordered breathing in accordance with embodiments of the invention.

FIGS. 5, 6, and 7 are graphs of transthoracic impedance and tidal volume, similar to FIG. 4 previously described. As stated earlier, using transthoracic impedance is one indirect method of determining brain state, such as by detecting sleep state, arousal, and disordered breathing, for example. As in FIG. 4, FIGS. 5, 6, and 7, illustrate the impedance signal 500 proportional to the transthoracic impedance, again illustrated as Impedance 530 on the abscissa of the left side of the graphs in FIGS. 5, 6, and 7. The impedance 530 increases during any respiratory inspiration 520 and decreases during any respiratory expiration 510. As before, the impedance signal 500 is also proportional to the amount of air inhaled, denoted the tidal volume 540, illustrated on the abscissa of the right side of the graph in FIGS. 5, 6, and 7. The magnitude of variations in impedance and tidal volume during respiration are identifiable as the peak-to-peak variation of the impedance signal 500.

FIG. 5 illustrates respiration intervals used for disordered breathing detection useful in accordance with embodiments of the invention. Respiration intervals are used to detect apnea and hypopnea, as well as provide other sleep-state information for activating therapy in accordance with embodiments of the present invention. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling.

Respiration intervals are established using an inspiration threshold 610 and an expiration threshold 620. The inspiration threshold 610 marks the beginning of an inspiration period 630 and is determined by the transthoracic impedance signal 500 rising above the inspiration threshold 610. The inspiration period 630 ends when the transthoracic impedance signal 500 is a maximum 640. The maximum transthoracic impedance signal 640 corresponds to both the end of the inspiration interval 630 and the beginning of an expiration interval 650. The expiration interval 650 continues until the transthoracic impedance 500 falls below an expiration threshold 620. A non-breathing interval 660 starts from the end of the expiration period 650 and continues until the beginning of a next inspiration period 670.

Detection of sleep apnea and severe sleep apnea is illustrated in FIG. 6. The patient's respiration signals are monitored and the respiration cycles are defined according to an inspiration 730, an expiration 750, and a non-breathing 760 interval as described in connection with FIG. 5. A condition of sleep apnea is detected when a non-breathing period 760 exceeds a first predetermined interval 790, denoted the sleep apnea interval. A condition of severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a condition of disordered breathing characterized by abnormally shallow breathing. Hypopnea reduces oxygen to the brain, and is linked with altered brain activity and brain states. The altered brain activity and brain states indicative of hypopnea may be used by a PIMD device to activate therapy in accordance with embodiments of the present invention. FIG. 7 is a graph of tidal volume derived from transthoracic impedance measurements. The graph of FIG. 7 illustrates the tidal volume of a hypopnea episode compared to the tidal volume of a normal breathing cycle illustrated previously in FIG. 4, which illustrated normal respiration tidal volume and rate. As shown in FIG. 7, hypopnea involves a period of abnormally shallow respiration, possible at an increased respiration rate.

Hypopnea is detected by comparing a patient's respiratory tidal volume 803 to a hypopnea tidal volume 801. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 7, a hypopnea episode 805 is identified when the average tidal volume is significantly below the normal tidal volume. In the example illustrated in FIG. 7, the normal tidal volume during the breathing process is identified as the peak-to peak value identified as the respiratory tidal volume 803. The hypopnea tidal volume during the hypopnea episode 805 is identified as hypopnea tidal volume 801. For example, the hypopnea tidal volume 801 may be about 50% of the respiratory tidal volume 803. The value 50% is used by way of example only, and determination of thresholds for hypopnea events may be determined as any value appropriate for a given patient.

In the example above, if the tidal volume falls below 50% of the respiratory tidal volume 803, the breathing episode may be identified as a hypopnea event, originating the measurement of the hypopnea episode 805.

Figure 8:
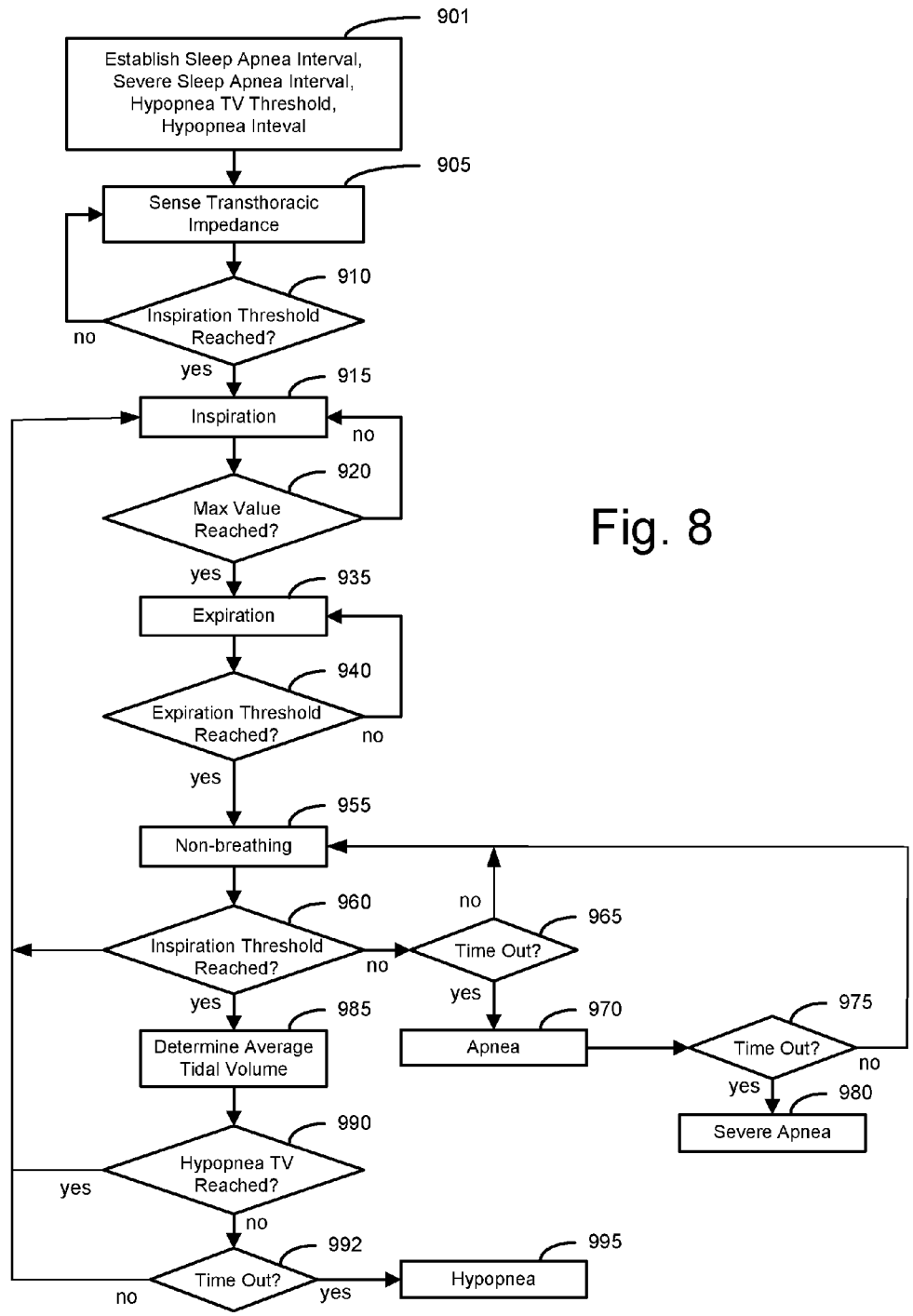
FIG. 8 is a flow chart illustrating a method of apnea and/or hypopnea detection according to embodiments of the invention.

FIG. 8 is a flow chart illustrating a method of apnea and/or hypopnea detection useful for cardiac resynchronization therapy for improved hemodynamics based on disordered breathing detection in accordance with the present invention. Various parameters are established 901 before analyzing the patient's respiration for disordered breathing episodes, including, for example, inspiration and expiration thresholds, sleep apnea interval, severe sleep apnea interval, and hypopnea tidal volume (TV) threshold.

The patient's transthoracic impedance is measured 905 as described in more detail above. If the transthoracic impedance exceeds 910 the inspiration threshold, the beginning of an inspiration interval is detected 915. If the transthoracic impedance remains below 910 the inspiration threshold, then the impedance signal is checked 905 periodically until inspiration 915 occurs.

During the inspiration interval, the patient's transthoracic impedance is monitored until a maximum value of the transthoracic impedance is detected 920. Detection of the maximum value signals an end of the inspiration period and a beginning of an expiration period 935.

The expiration interval is characterized by decreasing transthoracic impedance. When, at determination 940, the transthoracic impedance falls below the expiration threshold, a non-breathing interval is detected 955.

If the transthoracic impedance determination 960 does not exceed the inspiration threshold within a first predetermined interval, denoted the sleep apnea interval 965, then a condition of sleep apnea is detected 970. Severe sleep apnea 980 is detected if the non-breathing period extends beyond a second predetermined interval, denoted the severe sleep apnea interval 975.

When the transthoracic impedance determination 960 exceeds the inspiration threshold, the tidal volume from the peak-to-peak transthoracic impedance is calculated, along with a moving average of past tidal volumes 985. The peak-to-peak transthoracic impedance provides a value proportional to the tidal volume of the respiration cycle. This value is compared at determination 990 to a hypopnea tidal volume threshold. If, at determination 990, the peak-to-peak transthoracic impedance is consistent with the hypopnea tidal volume threshold for a predetermined time 992, then a hypopnea cycle 995 is detected.

Figure 9:
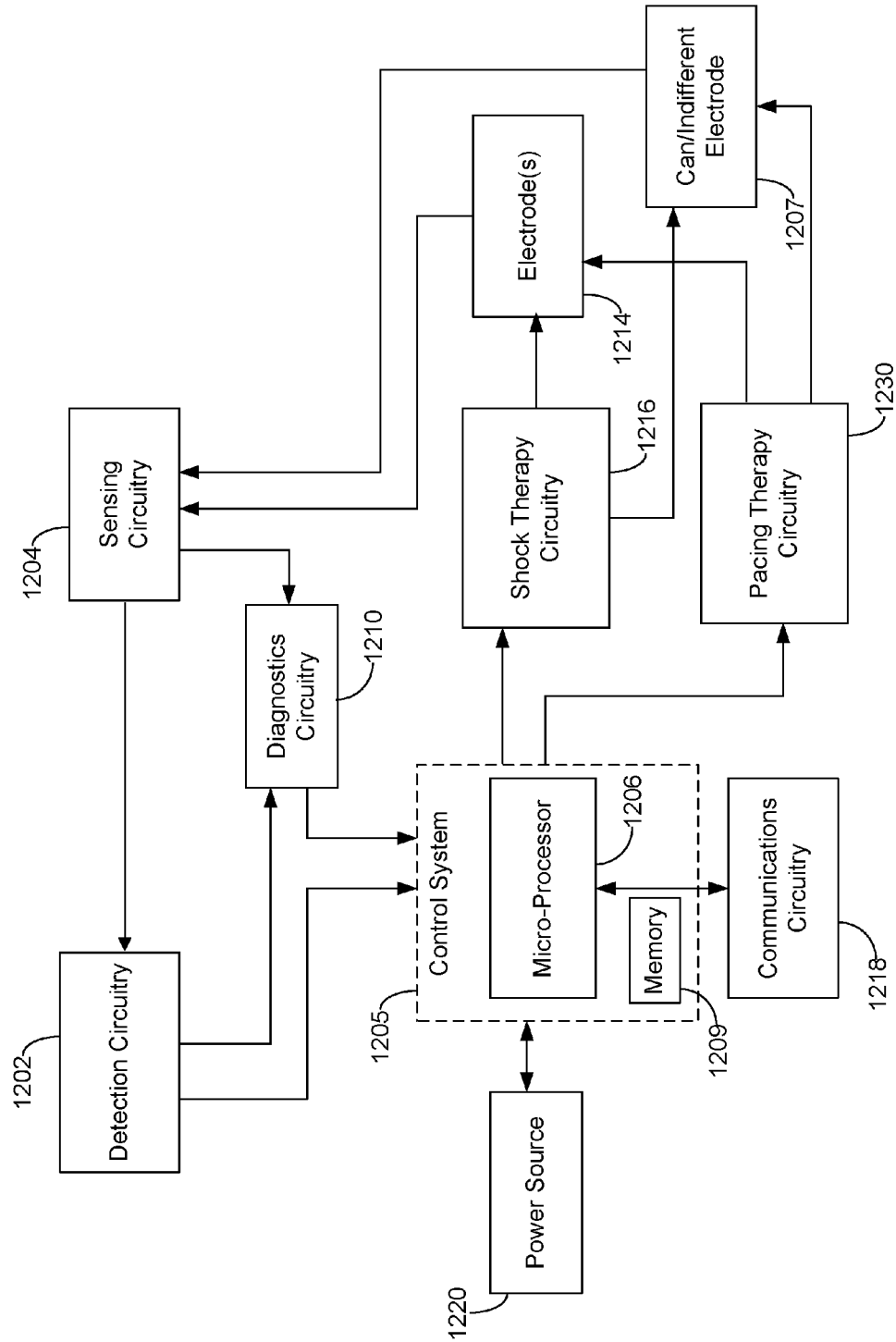
FIG. 9 is a block diagram illustrating various components of a cardiac monitoring and/or stimulation device in accordance with an embodiment of the present invention.

FIG. 9 is a block diagram depicting various componentry of different arrangements of a PIMD in accordance with embodiments of the present invention. The components, functionality, and configurations depicted in FIG. 9 are intended to provide an understanding of various features and combinations of features that may be incorporated in a PIMD. It is understood that a wide variety of device configurations are contemplated, ranging from relatively sophisticated to relatively simple designs. As such, particular PIMD configurations may include some componentry illustrated in FIG. 9, while excluding other componentry illustrated in FIG. 9.

Illustrated in FIG. 9 is a processor-based control system 1205 which includes a micro-processor 1206 coupled to appropriate memory (volatile and/or non-volatile) 1209, it being understood that any logic-based control architecture may be used. The control system 1205 is coupled to circuitry and components to sense, detect, and analyze electrical signals produced by the heart and deliver electrical stimulation energy to the heart under predetermined conditions to treat cardiac arrhythmias and/or other cardiac conditions. The control system 1205 and associated components also provide pacing therapy to the heart. The electrical energy delivered by the PIMD may be in the form of low energy pacing pulses or high-energy pulses for cardioversion or defibrillation.

Cardiac signals are sensed using the electrode(s) 1214 and the can or indifferent electrode 1207 provided on the PIMD housing. Cardiac signals may also be sensed using only the electrode(s) 1214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 1204, which includes sense amplification circuitry and may also include filtering circuitry and an analog-to-digital (A/D) converter. The sensed cardiac signals processed by the sensing circuitry 1204 may be received by noise reduction circuitry (not shown), which may further reduce noise before signals are sent to the detection circuitry 1202.

Detection circuitry 1202 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 1202 to detect and verify the presence and severity of an arrhythmic episode. Examples of arrhythmia detection and discrimination circuitry, structures, and techniques, aspects of which may be implemented by a PIMD in accordance with the present invention are disclosed in commonly owned U.S. Pat. Nos. 5,301,677, 6,438,410, and 6,708,058, which are hereby incorporated herein by reference. Arrhythmia detection methodologies particularly well suited for implementation in cardiac monitoring and/or stimulation systems are described hereinbelow.

The detection circuitry 1202 communicates cardiac signal information to the control system 1205. Memory circuitry 1209 of the control system 1205 contains parameters for operating in various monitoring, defibrillation, and, if applicable, pacing modes, and stores data indicative of cardiac signals received by the detection circuitry 1202. The memory circuitry 1209 may also be configured to store historical ECG and therapy data, which may be used for various purposes and transmitted to an external receiving device as needed or desired.

In certain configurations, the PIMD may include diagnostics circuitry 1210. The diagnostics circuitry 1210 typically receives input signals from the detection circuitry 1202 and the sensing circuitry 1204. The diagnostics circuitry 1210 provides diagnostics data to the control system 1205, it being understood that the control system 1205 may incorporate all or part of the diagnostics circuitry 1210 or its functionality. The control system 1205 may store and use information provided by the diagnostics circuitry 1210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 1205 processes cardiac signal data received from the detection circuitry 1202 and initiates appropriate tachyarrhythmia therapies to terminate cardiac arrhythmic episodes and return the heart to normal sinus rhythm. The control system 1205 is coupled to shock therapy circuitry 1216. The shock therapy circuitry 1216 is coupled to the electrode(s) 1214 and the can or indifferent electrode 1207 of the PIMD housing.

Upon command, the shock therapy circuitry 1216 delivers cardioversion and defibrillation stimulation energy to the heart in accordance with a selected cardioversion or defibrillation therapy. In a less sophisticated configuration, the shock therapy circuitry 1216 is controlled to deliver defibrillation therapies, in contrast to a configuration that provides for delivery of both cardioversion and defibrillation therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

As is shown in FIG. 9, the PIMD includes pacing therapy circuitry 1230 that is coupled to the control system 1205 and the electrode(s) 1214 and can/indifferent electrodes 1207. Upon command, the pacing therapy circuitry 1230 delivers pacing pulses to the heart in accordance with a selected pacing therapy.

Control signals, developed in accordance with a pacing regimen by pacemaker circuitry within the control system 1205, are initiated and transmitted to the pacing therapy circuitry 1230 where pacing pulses are generated. A pacing regimen may be modified by the control system 1205. In one particular application, a sense vector optimization may be implemented to enhance capture detection and/or capture threshold determinations, such as by selecting an optimal vector for sensing an evoked response resulting from application of a capture pacing stimulus.

The PIMD shown in FIG. 9 may be configured to receive signals from one or more physiologic and/or non-physiologic sensors. Depending on the type of sensor employed, signals generated by the sensors may be communicated to transducer circuitry coupled directly to the detection circuitry 1202 or indirectly via the sensing circuitry 1204. It is noted that certain sensors may transmit sense data to the control system 1205 without processing by the detection circuitry 1202.

Communications circuitry 1218 is coupled to the microprocessor 1206 of the control system 1205. The communications circuitry 1218 allows the PIMD to communicate with one or more receiving devices or systems situated external to the PIMD. By way of example, the PIMD may communicate with a patient-worn, portable or bedside communication system via the communications circuitry 1218. In one configuration, one or more physiologic or non-psyiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD via the communications circuitry 1218. It is noted that physiologic or non-physiologic sensors equipped with wireless transmitters or transceivers may communicate with a receiving system external of the patient.

The communications circuitry 1218 allows the PIMD to communicate with an external programmer. In one configuration, the communications circuitry 1218 and the programmer unit (not shown) use a wire loop antenna and a radio frequency telemetric link, as is known in the art, to receive and transmit signals and data between the programmer unit and communications circuitry 1218. In this manner, programming commands and data are transferred between the PIMD and the programmer unit during and after implant. Using a programmer, a physician is able to set or modify various parameters used by the PIMD. For example, a physician may set or modify parameters affecting monitoring, detection, pacing, and defibrillation functions of the PIMD, including pacing, resynchronization, and cardioversion/defibrillation therapy modes. The physician may, for example, modify pacing parameters or enable pacing therapies (e.g., CRT therapies) appropriate for a patient who has been identified as suitable for CRT therapy in a manner described herein. Enabling CRT therapies may, for example, involve downloading such therapies to the PIMD via a programmer, advanced patient management system, or other patient-external systems, or activating such therapies that may be stored (but previously unused) in PIMD memory.

Typically, the PIMD is encased and hermetically sealed in a housing suitable for implanting in a human body as is known in the art. Power to the PIMD is supplied by an electrochemical power source 1220 housed within the PIMD. In one configuration, the power source 1220 includes a rechargeable battery. According to this configuration, charging circuitry is coupled to the power source 1220 to facilitate repeated non-invasive charging of the power source 1220. The communications circuitry 1218, or separate receiver circuitry, is configured to receive RF energy transmitted by an external RF energy transmitter. The PIMD may, in addition to a rechargeable power source, include a non-rechargeable battery. It is understood that a rechargeable power source need not be used, in which case a long-life non-rechargeable battery is employed.

The detection circuitry 1202, which is coupled to a microprocessor 1206, may be configured to incorporate, or communicate with, specialized circuitry for processing sensed cardiac signals in manners particularly useful in a cardiac sensing and/or stimulation device. As is shown by way of example in FIG. 9, the detection circuitry 1202 may receive information from multiple physiologic and non-physiologic sensors.

The detection circuitry 1202 may also receive information from one or more sensors that monitor skeletal muscle activity. In addition to cardiac activity signals, electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise.

The components, functionality, and structural configurations depicted herein are intended to provide an understanding of various features and combination of features that may be incorporated in a PIMD. It is understood that a wide variety of PIMDs and other implantable cardiac monitoring and/or stimulation device configurations are contemplated, ranging from relatively sophisticated to relatively simple designs. As such, particular PIMD or cardiac monitoring and/or stimulation device configurations may include particular features as described herein, while other such device configurations may exclude particular features described herein.

The PIMD may detect a variety of physiological signals that may be used in connection with various diagnostic, therapeutic or monitoring implementations. For example, the PIMD may include sensors or circuitry for detecting respiratory system signals, cardiac system signals, and signals related to patient activity. In one embodiment, the PIMD senses intrathoracic impedance, from which various respiratory parameters may be derived, including, for example, respiratory tidal volume and minute ventilation. Sensors and associated circuitry may be incorporated in connection with a PIMD for detecting one or more body movement or body posture or position related signals. For example, accelerometers and GPS devices may be employed to detect patient activity, patient location, body orientation, or torso position.

A PIMD in accordance with the present invention may be used within the structure of an advanced patient management (APM) system. The advanced patient management system allows physicians to remotely and automatically monitor cardiac and respiratory functions, as well as other patient conditions. In one example, a PIMD implemented as a cardiac pacemaker, defibrillator, resynchronization device, cardiac neurostimulation device, or other implantable medical monitoring, diagnostic, or therapy device may be equipped with various telecommunications and information technologies that enable real-time data collection, diagnosis, and/or treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable medical device, comprising:
   a housing configured for implantation in a patient; and
   a processor provided in the housing and configured to:
   detect presence of sleep disordered breathing;
   detect a level of cardiac dyssynchrony at least one of within and between cardiac chambers of the patient; and
   identify if the patient is likely to respond to a cardiac resynchronization therapy based on the presence of disordered breathing and the level of the cardiac dyssynchrony.

2. The device of claim 1, wherein the processor is further configured to initiate cardiac resynchronization therapy for the patient based on the combined detection of the sleep disordered breathing and the level of the cardiac dyssynchrony.

3. The device of claim 2, further comprising:
   a pulse generator coupled to the processor;
   wherein the processor is also configured to enable the pulse generator to deliver the cardiac resynchronization therapy, and wherein enabling comprises at least one of downloading cardiac resynchronization therapy protocol to the implantable medical device, and activating unused cardiac resynchronization therapy protocol stored in memory of the implantable medical device.

4. The device of claim 1, wherein the processor is configured to adjust an atrioventricular delay based on the type of sleep disordered breathing detected by the implantable medical device.

5. The device of claim 1, wherein the processor is configured to detect a QRS complex width exceeding a predetermined value and measure an apnea/hypopnea index exceeding a predetermined value.

6. The device of claim 1, further comprising an implantable sensor arrangement coupled to the implantable medical device, the processor configured to detect a ventricular dyssynchrony in the patient's heart via the implantable sensor arrangement.

7. The device of claim 1, further comprising a patient-external sensor arrangement coupled to the implantable medical device, the processor configured to detect a ventricular dyssynchrony in the patient's heart via the patient-external sensor arrangement.

8. The device of claim 1, wherein the processor is coupled to communication circuitry configured to facilitate wireless communication between the processor and a patient-external device or system.

9. The device of claim 8, wherein the patient-external device or system is configured to generate a clinician alert to initiate, terminate, adjust, or optimize the cardiac resynchronization therapy based on the combined detection of the sleep disordered breathing and the cardiac dyssynchrony.

10. The device of claim 5, wherein the processor is configured to detect a QRS complex width exceeding 120 milliseconds and measure an apnea/hypopnea index value exceeding 15 episodes per hour.

11. The device of claim 1, wherein the detected cardiac dyssynchrony is an impaired left-ventricular function that is not reflected in the patient's general functional status as assessed by New York Heart Association (NYHA) functional class.

12. A system, comprising:
    a housing configured for implantation in a patient; and
    a processor provided in the housing and configured to:
    detect presence of sleep disordered breathing;
    detect a level of cardiac dyssynchrony at least one of within and between cardiac chambers of the patient;
    identify if the patient is likely to respond to a cardiac resynchronization therapy based on the presence of disordered breathing and the level of the cardiac dyssynchrony; and
    if the patient is identified as likely to respond, provide or alter cardiac resynchronization therapy for the patient based on the combined detection of the sleep disordered breathing and the level of the cardiac dyssynchrony.

13. The system of claim 12, wherein the system comprises a pulse generator and electrodes that are configured to be arranged in multiple heart chambers of the patient for cardiac resynchronization therapy delivery.

14. The system of claim 12, wherein the processor is configured to adjust an atrioventricular delay based on a type of the sleep disordered breathing detected.

15. A method, comprising:
    detecting presence of sleep disordered breathing using a processor within an implantable medical device in a patient;
    detecting a cardiac dyssynchrony at least one of within and between cardiac chambers of the patient using the processor; and
    determining if the patient is likely to respond to cardiac resynchronization therapy based on a level of the cardiac dyssynchrony using the processor.

16. The method of claim 15, further comprising initiating cardiac resynchronization therapy for the patient based on the combined detection of the sleep disordered breathing and the cardiac dyssynchrony and the determination.

17. The method of claim 15, wherein detecting presence of sleep disordered breathing comprises detecting at least one of obstructive sleep apnea, central sleep apnea, hypopnea, orthopnea, paroxysmal nocturnal dyspnea, and Cheyne-Stokes respiration.

18. The method of claim 15, further comprising:
    enabling the implantable medical device to perform the cardiac resynchronization therapy based on the combined detection of the sleep disordered breathing and the cardiac dyssynchrony, wherein the enabling comprises at least one of downloading a cardiac resynchronization therapy protocol to the implantable medical device, and activating an unused cardiac resynchronization therapy protocol stored in memory of the implantable medical device.

19. The method of claim 15, wherein detecting the presence of sleep disordered breathing comprises measuring an apnea/hypopnea index exceeding a predetermined value, and wherein detecting the cardiac dyssynchrony comprises detecting a QRS complex width exceeding a predetermined value.

20. The method of claim 15, wherein detecting the cardiac dyssynchrony comprises one or more of detecting left ventricular systolic dysfunction, detecting a left ventricular systolic dysfunction comprising a left ventricular ejection fraction value less than a predetermined limit, determining that a QRS complex width of a cardiac cycle exceeds a predetermined limit, and detecting a ventricular wall motion asynchrony that exceeds a predetermined limit.

* * * * *